United States Patent [19]
DeBonville et al.

[11] Patent Number: 5,204,257
[45] Date of Patent: Apr. 20, 1993

[54] METHOD OF RECOVERING BACTERIOPHAGE

[75] Inventors: David A. DeBonville, Beverly; Kelley A. Logan, Somerville, both of Mass.

[73] Assignee: Autogen Instruments, Inc., Beverly, Mass.

[21] Appl. No.: 693,133

[22] Filed: Apr. 29, 1991

[51] Int. Cl.$^5$ .......................... C12N 7/02; C07K 3/12
[52] U.S. Cl. .................................... 435/239; 530/412; 530/417; 530/821; 530/826; 935/19
[58] Field of Search ................ 435/239, 5; 530/821, 530/826, 417, 412 T; 935/19; 536/27

[56] References Cited

U.S. PATENT DOCUMENTS 4,923,978   5/1990   McCormick ..................... 536/27

OTHER PUBLICATIONS

Luthe et al., *Plant Phys.*, (1980), vol. 65, pp. 305–308.
Sambrook et al. *Molecular Cloning* (2nd Ed.), 1989, p. 2.73.

*Primary Examiner*—Robert A. Wax
*Assistant Examiner*—Keith D. Hendricks
*Attorney, Agent, or Firm*—Iandiorio & Dingman

[57] ABSTRACT

A method of recovering nucleic acid-containing particles from a liquid medium by contacting the liquid medium containing the particles with a mixture of hydroxylated silica beads and a salt solution to bind the nucleic acid-containing particles, centrifuging the mixture to pellet the bound particles, and separating the pellet from the liquid.

17 Claims, No Drawings

METHOD OF RECOVERING BACTERIOPHAGE

FIELD OF INVENTION

This invention relates to a method of recovering bacteriophage from solutions of cell media which can be used in manual or automated nucleic acid purification procedures.

BACKGROUND OF INVENTION

The isolation and analysis of nucleic acids from various biological sources is a commonly performed procedure in genetic and recombinant DNA research. As the primary genetic elements, nucleic acids will exist in various forms depending on the biological source. In the case of bacteriophages and viruses, which contain single- or double-stranded DNA or RNA, purification of nucleic acids require that the intact bacteriophage or virus particles can be recovered from the cell culture media prior to performing the nucleic acid purification steps. The procedures and chemistries commonly employed for recovering bacteriophage or viral particles prior to isolation of nucleic acids are described in detail in T. Maniatis et al.: *Molecular Cloning—A Laboratory Manual*, Cold Spring Harbor (1989).

In standard manual bacteriophage nucleic acid preparations the cells are separated from the bacteriophage particles by differential centrifugation. The cell-free media is transferred to a separate vessel and a precipitating agent of polyethylene glycol/sodium chloride is added to the media and mixed. The resulting solution is incubated at reduced temperature, typically 4 degrees C., for one hour or more. To insure efficient recovery of DNA, long incubations, from several hours to over night, at reduced temperatures with polyethylene glycol, are emphasized. To insure recovery of high quality DNA, incubation in the presence of protein digesting enzymes is also emphasized. Samples are then centrifuged at high speed at 4 degrees C. to recover the bacteriophage/polyethylene glycol/sodium chloride complexes. The media is aspirated and discarded, leaving the bacteriophage pellet behind. The bacteriophage are resuspended in digestion buffer and treated with protein digesting enzymes for several hours at elevated temperatures. Following this digestion, the sample is extracted repeatedly with phenol and chloroform to remove contaminating material. Nucleic acids in the resulting solution are mixed with ethanol and centrifuged to concentrate the nucleic acids. The nucleic acid pellet is washed, dried briefly and resuspended in a small volume of buffer.

In both automatic and manual DNA separation techniques, these extensive manipulations are time consuming and inefficient, making nucleic acid purification an expensive procedure.

SUMMARY OF INVENTION

It is therefore an object of this invention to provide a simplified method for recovering nucleic acid-containing bacteriophage particles from cell media solutions to facilitate nucleic acid purification from bacteriophage.

It is a further object of this invention to provide such a method which employs the mixing processes of automated DNA separation techniques.

It is a further object of this invention to provide such a method which when applied to automated separation techniques provides high quality results.

This invention results from the realization that manual and automated DNA separation techniques from bacteriophage sources can be dramatically improved by recovering the bacteriophage particles using a hydroxylated silica/salt complex at room temperature.

This invention features a method of recovering nucleic acid-containing particles such as bacteriophage particles from a liquid medium such as a cell-containing nutrient broth. The method contemplates contacting the liquid medium with a mixture of a salt solution and a hydroxylated silica to bind the nucleic acid-containing particles, centrifuging the resultant mixture to pellet the bound particles, and separating the pellet from the liquid.

The salt in solution may be a chloride salt such as sodium chloride, potassium chloride, or lithium chloride, or an acetate salt. Preferably, the concentration of the salt in the silica bead/salt/phage mixture is from 0.5 to 2.0M. All the steps of the separation procedure may be accomplished at room temperature.

The method may also include the step of incubating the liquid medium/salt/silica mixture before centrifugation for from one to ten minutes. The centrifugation preferably takes place at at least 500 rpm for at least one minute; in a preferred embodiment, the mixture is centrifuged at about 8000 rpm for about two minutes to pellet the silica bead/salt/particle complex. The liquid containing the contaminants may then be removed by aspiration.

DISCLOSURE OF PREFERRED EMBODIMENT

Other objects, features and advantages will occur to those skilled in the art from the following description of a preferred embodiment.

This invention may be accomplished in a method for room temperature recovery of bacteriophage particles from cell media solutions, in which a high ionic strength hydroxylated silica/salt precipitating agent is added to a solution of bacteriophage particles, mixed, and the resulting solution centrifuged to recover the bacteriophage/silica/salt complex prior to isolation and purification of nucleic acids. As a result, lengthy incubations at reduced temperature and extensive treatment with deproteinating agents are obviated in both manual and automated nucleic acid preparation procedures. As an example, the known manual protocols, run at room temperature (65° to 75° F.), yield only about 30%–50% of the DNA extracted using the room-temperature protocol of this invention. This invention may thus simply and quickly accomplish preparations at least as good as the longer and more laborious manual separation techniques.

EXAMPLE I

Preparation of the Hydroxylated Silica/Salt Solution Mixture

The separation of the nucleic acid-containing particles from a liquid medium such as a cell-containing nutrient broth is accomplished with a combination of hydroxylated silica such as US Bioclean glass powder, United States Biochemical, Cleveland, Ohio, and Strataclean resin, Stratagene, La Jolla, Calif., and a salt solution such as a chloride or acetate salt, creating a high ionic strength mixture; the hydroxylated silica or salt alone will not precipitate the phage.

In an experiment designed to optimize DNA yield from bacteriophage, varying amounts of hydroxylated glass beads and salt solutions of different composition and concentration were mixed with solutions containing bacteriophage M13. Included as controls were bacteriophage M13 samples mixed with hydroxylated glass beads in the absence of high salt, and bacteriophage M13 samples mixed with high salt in the absence of hydroxylated glass beads. For comparison, the manual purification method employing polyethylene glycol was included as an internal standard. DNA yields were considered optimal when the yields obtained with hydroxylated glass beads and high salt were comparable to the internal standard prepared by the polyethylene glycol method. By comparison, control experiments where hydroxylated glass beads and high salt were not used in conjunction did not yield any detectable amounts of bacteriophage DNA.

As described in U.S. Pat. No. 4,923,978, incorporated herein by reference, the hydroxylated silica may be in the form of five to ten micron beads with pores of tens to hundreds of angstroms in diameter. The beads also have surface hydroxyl groups. In the cited patent, the beads alone are used to bind the contaminating protein material to leave behind unbound nucleic acids. It has been found herein that when the beads are mixed with a salt solution, the resultant mixture is able to bind bacteriophage particles to simplify their isolation from liquid solutions. Hydroxylated silica beads exhibiting the same purification properties as the commercially available hydroxylated silica have been fabricated as follows:

300 ml of 325-mesh powdered flint glass, (Cutter Ceramics, Beltsville, N.J.), was measured out into a beaker. 300 ml of distilled water was added, and the mixture mixed to break up the chunks until a homogeneous liquid was obtained. The liquid was mixed with stir bar on a magnetic stirrer for one hour at room temperature. The mixture was then allowed to stand at room temperature for one hour to settle the heavier material and debris. The supernatant was then transferred to a centrifuge tube large enough to accommodate the liquid (approximately 250 ml), without transferring any of the settled material. The sample was centrifuged in an RC-3B centrifuge for twenty minutes at 2500 RPM, and the supernatant was discarded. The pellet was resuspended in 200 ml of distilled water in a glass beaker. Under a hood, 250 ml of nitric acid (Aldrich, Cat. #25,811-3, Nitric acid, 70%, A.C.S. reagent) was added. The mixture was heated with gentle stirring to almost boiling (110° C. for five minutes). The solution was allowed to cool to room temperature (approximately one to two hours). During this time the glass beads settled. The supernatant was then carefully removed, avoiding settled glass beads, and discarded. 300 ml of distilled water was added, the contents mixed, transferred to centrifuge tubes, and the glass beads were pelleted by centrifugation. The supernatant was discarded. The distilled water wash and pelleting was repeated three more times for a total of four washes with distilled water. After decanting the last wash, the volume of pelleted glass beads was estimated, and an equal volume of distilled water was added, and mixed vigorously to resuspend the glass beads. The resultant glass bead preparation can be stored at 4° C. as a 50% slurry.

The glass bead/salt mixture was prepared in advance in a tube into which a known volume of nutrient broth containing bacteriophage particles was aspirated as described below in Examples II and III. For small scale preparations, glass bead/salt mixtures were prepared by adding approximately 100 μl of a 50% slurry of hydroxylated glass beads and approximately 300 μl of a salt solution, such as a chloride or acetate salt, at a concentration of 2 to 8 molar salt. To this, 800 μl of liquid containing bacteriophage particles was added to make a total reaction volume of 1200 μl.

It has been found, based on a total reaction volume of 1200 μl, that nucleic acid containing particles were efficiently recovered with final salt concentrations of 0.5 to 3 molar with a 2 molar solution being optimal. Raising the final salt concentration above 2 molar did not improve particle recovery. It has also been found that recovery was possible with as little as 5 μl of glass bead, with 100 μl being optimal. The method of this invention describes small scale preparations of nucleic acid containing particles but could be appropriately modified and applied to large scale preparations also.

EXAMPLE II

M13 Single-Stranded Isolation Protocol

The separation method of this invention has been used in isolating single-stranded DNA from bacteriophage M13 as follows:

Cultures containing *E. coli* bacterial cells and M13 bacteriophage were centrifuged at 8000 rpm for two minutes to pellet the cells. 800 microliters of the nutrient broth containing the M13 was aspirated to a second tube containing 100 microliters of the hydroxylated silica beads and 300 microliters of lithium chloride solution of 2 molar concentration in the final solution (8 molar to start), and mixed by repeated pipetting.

Following a ten minute incubation at room temperature, the mixture was centrifuged at 8000 rpm for two minutes at room temperature to concentrate the silica/salt/bacteriophage complexes. The supernatant was discarded leaving the pellet behind. 600 μl of a buffer was added and the samples were mixed by pipetting to resuspend the pellet.

The samples were extracted once with 300 μl of phenol/chloroform to remove contaminants and then centrifuged at 8000 rpm for three minutes to separate organic and aqueous phases.

The aqueous phase was transferred to a third tube containing 100 microliters of 3M potassium acetate and 500 microliters of 50:50 isopropanol:ethanol and mixed. The DNA was pelleted by centrifuging at 8000 rpm for three minutes at room temperature, and the supernatant discarded. 1 ml of 70% ethanol was added to wash the DNA pellet. The supernatant was removed, and the pellet dried briefly and resuspended in 50 microliters buffer.

The result was single-stranded M13 DNA in yield and quality at least as good as that of the manual procedure employing the polyethylene glycol treatment at 4° C. and repeated extraction with phenol and chloroform.

EXAMPLE III

Phagemid Single-Stranded Isolation Protocol

The separation method of this invention has been used in isolating single-stranded DNA from phagemids as follows:

Cultures containing *E. coli* bacterial cells and phagemid bacteriophage were centrifuged at 8000 rpm for two minutes. The nutrient broth was aspirated to a second tube and mixed with a hydroxylated silica/lithium chloride solution.

Following a ten minute incubation at room temperature, the mixture was centrifuged at 8000 rpm for two minutes to concentrate the silica/salt/phagemid complexes. The supernatant was discarded leaving the pellet behind. A buffer was added and the samples were mixed to resuspend the pellet.

The samples were extracted once with a deproteinating solution of phenol/chloroform to remove contaminants and then centrifuged at 8000 rpm for three minutes to separate organic and aqueous phases.

The aqueous phase was transferred to a third tube and mixed with ethanol to precipitate the DNA. The DNA precipitate was concentrated by centrifugation at 8000 rpm for three minutes. The DNA pellet was washed, dried briefly and resuspended as described above.

The result was single-stranded phagemid DNA in yield and quality at least as good as that of the manual procedure employing the polyethylene glycol treatment at 4° C. followed by enzymatic protein digestion and repeated extraction with phenol and chloroform.

When applied to the isolation of bacteriophage DNA in the above examples, the method of this invention replaced the long incubation with a substantially shorter one and eliminated the need for refrigeration. In addition, enzymatic digestions and the repeated performance of the protein extraction step of the manual procedure is obviated.

The procedure of this invention thus accomplishes substantially the same results as the manual isolation techniques in a technique adapted for automated processing equipment, where the reduced temperature and large number of tubes required for the known protocol would be impractical, thereby saving substantial technician's time. Thus, the method of this invention allows the separations to be performed on an automated machine with quality levels as good as those provided in the manual methods without the variability of results inherit in the manual separation techniques.

In further experimental work, it was found that at acidic pH, recovery was only 10% to 20% of the total bacteriophage particles. Recovery was very efficient at essentially neutral pH.

It has also been found that the complexing of the particles with the silica bead/salt solution is virtually instantaneous; experiments comparing incubation times of 1, 5, 10 and 20 minutes prior to recovering phage complex by centrifugation indicated that identical yields of DNA were obtained.

Accordingly, the method of this invention provides for DNA separation from phage particles with yields as good as the manual techniques, which require the use of five tubes per sample, a lengthy incubation at reduced temperature, and repeated organic extractions. In contrast, using the method of this invention, the same extraction may be accomplished in manual or automated techniques performed at room temperature using only three tubes and a single organic extraction. Accordingly, the method is simpler, faster, and less expensive than previous methods.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. A method of recovering bacteriophage from a liquid medium, comprising:
   contacting a liquid medium containing bacteriophage with a mixture of at least 0.5 molar inorganic chloride salt or acetic salt solution and a hydroxylated silica to bind the bacteriophage;
   centrifuging the resultant mixture to pellet the bound bacteriophage; and
   separating the pellet from the liquid.

2. The method of claim 1 in which the steps are performed at room temperature.

3. The method of claim 1 in which contacting the liquid medium with said mixture of salt solution and silica includes mixing the mixture after contacting to improve binding.

4. The method of claim 1 further including incubating the liquid medium/salt/silica mixture before centrifugation.

5. The method of claim 4 in which the mixture is incubated for at least one minute.

6. The method of claim 5 in which the mixture is incubated for approximately one to ten minutes.

7. The method of claim 4 in which the incubation is at room temperature.

8. The method of claim 1 in which the mixture is centrifuged at at least 500 rpm.

9. The method of claim 8 in which, the mixture is centrifuged for at least one minute.

10. The method of claim 9 in which the mixture is centrifuged at approximately 8000 rpm for approximately two minutes.

11. The method of claim 1 in which the separation is accomplished by aspiration.

12. The method of claim 1 in which said salt solution is a chloride salt solution.

13. The method of claim 12 in which the chloride salt is taken from the group including sodium chloride potassium chloride, and lithium chloride.

14. The method of claim 1 in which said salt solution is an acetate salt solution.

15. The method of claim 1 in which said salt solution is 0.5 to 2.0M.

16. The method of claim 1 in which the bacteriophage is taken from the group including M13 and phagemids.

17. A method of recovering bacteriophage from liquid broth medium, comprising:
   mixing a liquid medium containing bacteriophage with a 0.5 to 2.0M inorganic chloride salt or acetic salt solution/hydroxylated silica mixture to bind the bacteriophage;
   incubating the mixture;
   centrifuging the incubated mixture to pellet the bound bacteriophage; and
   separating the pellet from the liquid.

* * * * *